(12) United States Patent
You

(10) Patent No.: US 8,932,198 B1
(45) Date of Patent: Jan. 13, 2015

(54) ACUPUNCTURE DEVICE FOR SLEEPING DISORDERS

(76) Inventor: Tuming You, Xiamen (CN)

(*) Notice: Subject to any disclaimer, the term of this patent is extended or adjusted under 35 U.S.C. 154(b) by 250 days.

(21) Appl. No.: 13/341,879

(22) Filed: Dec. 30, 2011

(51) Int. Cl.
*A61H 39/00* (2006.01)
*A61H 33/06* (2006.01)
*A61H 39/08* (2006.01)
*A61B 17/54* (2006.01)

(52) U.S. Cl.
CPC .............. *A61B 17/545* (2013.01); *A61H 39/00* (2013.01)
USPC .......................................................... 600/27

(58) Field of Classification Search
CPC .................. A61H 2201/0207; A61H 15/0092; A61H 35/00; A61H 2201/025; A61H 2201/0257; A61H 2205/12; A61H 35/006; A61H 33/12; A61H 39/00
USPC ............................................................ 600/27
See application file for complete search history.

(56) References Cited

U.S. PATENT DOCUMENTS

| | | | |
|---|---|---|---|
| 6,755,398 B1 * | 6/2004 | Wong | 261/81 |
| 7,634,176 B2 * | 12/2009 | You | 392/386 |
| 2006/0195979 A1 * | 9/2006 | Liu | 4/535 |

OTHER PUBLICATIONS

"Sleep Solutions from Chinese Masters." Ni. Acupuncture.com Apr. 2010, vol. 8, Issue 4.*
Steam Good device—http://www.tachisan.com/Steamgood.htm. Oct. 3, 2011.*

* cited by examiner

*Primary Examiner* — Christine Matthews
*Assistant Examiner* — Joshua D Lannu
(74) *Attorney, Agent, or Firm* — DLA Piper LLP (US)

(57) ABSTRACT

Provided in the present invention is a method of providing treatment for a sleeping disorder.

17 Claims, 11 Drawing Sheets

MERIDIANS DIAGRAM

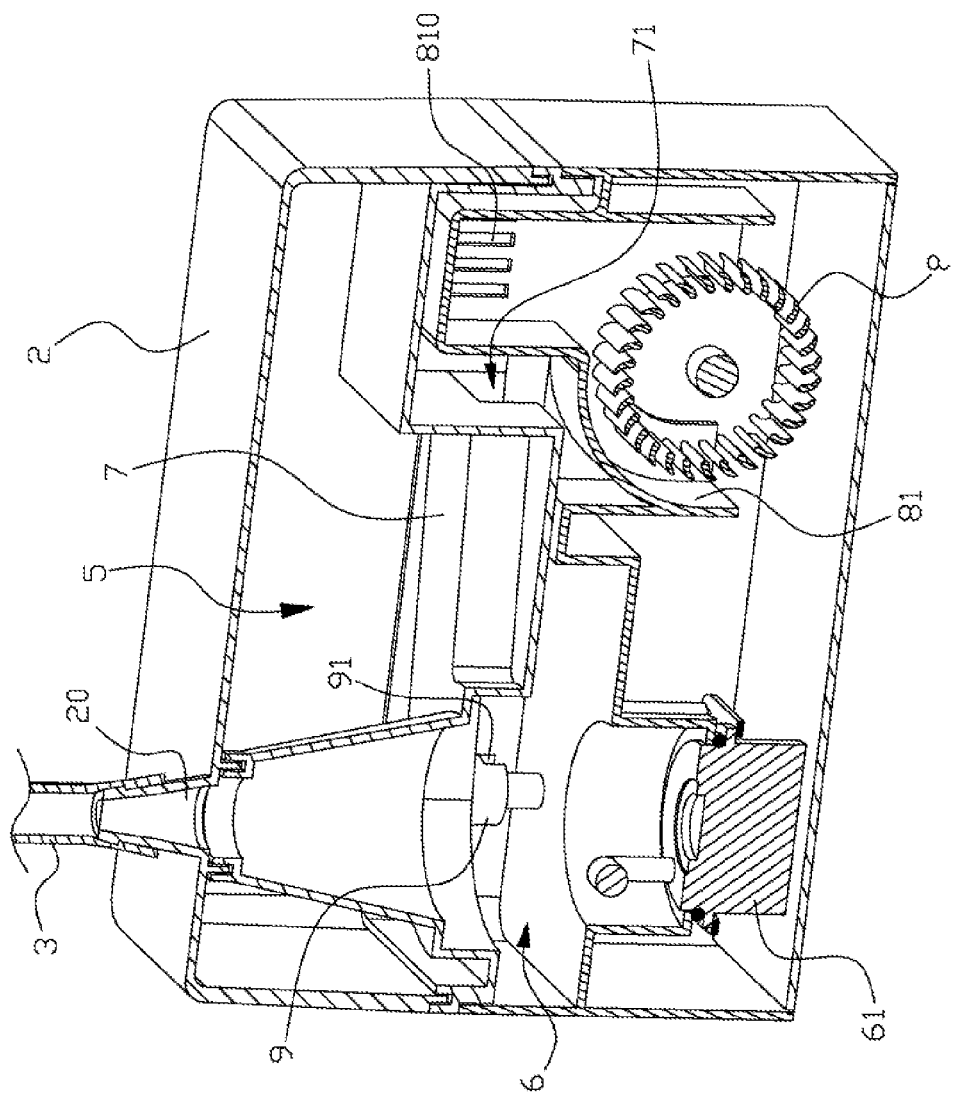
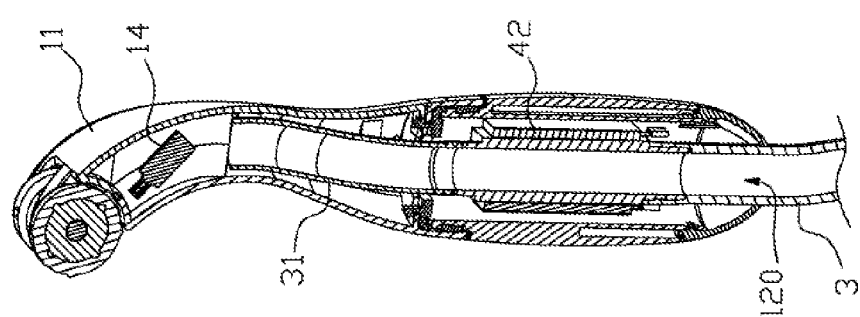
FIG. 2G
FIG. 2F

ACUPUNCTURE DEVICE FOR SLEEPING DISORDERS

FIELD OF THE INVENTION

The invention is related to an acupuncture device, specifically an acupuncture device for sleeping disorders.

BACKGROUND OF THE INVENTION

A sleeping disorder is associated with diseases such as diabetes, cancer, and many other diseases and is a major health risk factor in throughout the world. Many efforts are devoted to contain the spread of a sleeping disorder with limited success.

Traditional Chinese medicine focuses on interconnectedness and free flow of the biological system of a human being and believes any interference, e.g., blocking, with such a free flow biological system would result in a disorder of the biological system.

According to traditional Chinese medicine, blocking of the free flow of human biological system happens in certain places (points) in the human body and cause diseases to occur. A particular disorder corresponds to blocking of a particular point or set of points in the biological system. Stimulating one of these points can free up the flow of biological system of human being so as to treat or ameliorate a disease arising out of blocking of such point or set of points. According to this school of medicine, a method of therapeutics—acupuncture—was developed and practiced in China for thousands of years. The oldest medical book known, written in China 4000 years ago, describes the use of acupuncture to treat medical problems. The use of the treatment spread to other Asian countries and to other regions of the world, including to Europe by the 1700s. In the United States, acupuncture has been used for about 200 years.

Research on acupuncture began in the United States in 1976. Twenty years later, according to National Cancer Institute, the US Food and Drug Administration (FDA) approved the acupuncture needle as a medical device. Many illnesses are treated with acupuncture, but it is used mainly to control pain, including pain in cancer patients and to help control nausea and vomiting. Its primary use in cancer patients has been seen as an addition to conventional (standard) therapy.

The FDA approved acupuncture needles for use by licensed practitioners in 1996. The FDA requires that sterile, nontoxic needles be used and that they be labeled for single use by qualified practitioners only.

More than 40 states and the District of Columbia have laws regulating acupuncture practice. The National Certification Commission for Acupuncture and Oriental Medicine certifies practitioners of acupuncture and traditional Chinese medicine (TCM). Most states require this certification.

A common side effect of acupuncture is concern of infection caused by cross-contamination of acupuncture needles that may include viral or bacterial pathogens. Other concerns may arise out of patient's negative reactions against piercing of acupuncture needles or misapplication of such needles by a practitioner. Further, access to acupuncture by a practitioner is limited so as to limit the effect of acupuncture.

Therefore, there is a need for additional treatment regime for a sleeping disorder.

The embodiments described below address the above identified needs and issues.

SUMMARY OF THE INVENTION

In one aspect, it is provided a method of providing treatment of a sleeping disorder. The method comprises applying a stream of low temperature vapor to a set of acupoints or an acupoint when one feels hungry for a period of time in a course of treatment, thereby improving condition of a sleeping disorder or ameliorating symptoms of a sleeping disorder.

In some embodiments, the sleeping disorder is insomnia. Acupoints for a sleeping disorder include fengchi, yongquan, and shimian.

In some embodiments, the low temperature vapor steam is generated by a steam forming device described in U.S. Pat. No. 7,634,176, the teaching of which is incorporated herein in its entirety by reference.

In some embodiments, the steam forming device comprises (a) an atomization device comprising:
an atomizing chamber comprising a low temperature vapor outlet,
an atomizer which is located in the atomizing chamber to make the water become a low temperature vapor, and
an impeller driving the low temperature vapor of the atomizing chamber into the outlet;

(b) a high temperature steam forming device for producing high temperature steam comprising a high temperature steam outlet;

(c) a steam outlet pipe, comprising:
two steam intakes which are respectively connected with the low temperature vapor outlet of the atomizing chamber and high temperature steam outlet of the high temperature steam forming device, and
a mixing steam outlet; and (d) a water tank for supplying needed water for the atomization device and the high temperature steam forming device,
wherein a stream of water from the water tank passes through the atomizing device to generate a low temperature vapor,
wherein another stream of water from the water tank passes through the steam forming device to generate a high temperature steam,
wherein the high temperature steam and the low temperature vapor are mixed by the steam outlet pipe, and
wherein the composition of the mixed steam is adjusted by adjusting the proportions of the high temperature steam and the low temperature vapor.

In some embodiments, in the steam forming device of the above embodiments, the water tank comprises:
a main water tank located on the upper side,
an assistant water tank located on the lower side,
a water inlet valve between the main water tank and the assistant water tank, and
a wind guiding shell comprising a wind blowing mouth,
wherein the atomizing chamber is set on one side of and connected with the assistant;
wherein the low temperature steam outlet is set on the top of the atomizing chamber;
wherein the wind guiding shell is set outside of the impeller, the wind blowing mouth of the wind guiding shell facing the bottom of the low temperature steam outlet; and
wherein the water inlet pipe of the high temperature steam forming device is connected with the bottom of the assistant water tank where a water volume adjusting valve being set on the connecting area and the water volume adjusting valve comprises a knob which is adjustable outside.

In some embodiments, in the steam forming device of the above embodiments, the water inlet valve includes a cylinder valve body which is protruding into the assistant water tank from the bottom of the main water tank, wherein the bottom edge of the valve comprises a void, the position of the void being lower than the position of the wind blowing mouth;

wherein the valve comprises a valve hole in the middle of the valve body;

wherein in the valve hole there is a valve stopper which tightly fills the valve hole from the bottom to the top;

wherein the stopper comprises an up-extending valve stick on the top of the stopper, the valve stick comprising a spring causing the valve stick to move up to tightly fill the valve hole; and wherein the main water tank comprises a water inlet on the top of the main water tank, the water inlet comprises a knob cover, the bottom of which comprises a connecting rod which extends into the main water tank and is capable of pushing the valve stick downward so as to cause the valve stopper to pull away from the valve hole.

In some embodiments, in the steam forming device of above embodiments, wherein the mixing steam outlet of the steam guiding output pipe is connected with a hollow ring by a steam pipe, wherein on the bottom of the hollow ring there are many steam ejecting holes along the circumference, and wherein the hollow ring is set on a rack.

In some embodiments, in the steam forming device of above embodiments, wherein there is a heating unit located on the jointing position of the steam pipe and the hollow ring, wherein the heating unit comprises:
a metal pipe tie-in comprising two ends, the two ends being connected with the steam pipe,
a PTC heating element set on the outside wall of the metal pipe tie-in, and
a thermostat which is connected with the PTC heating element.

In some further embodiments of the method, the steam forming device is equipped to provide steam of adjustable temperature, the device comprises:

(a) an atomization device comprising:
an atomizing chamber,
an atomizer located in the atomizing chamber for causing water to become to low temperature vapor, and
an impeller for driving the low temperature vapor in the atomizing chamber to flow toward outlet;
(b) a water tank for supplying water to the atomization device;
(c) an output part comprising a handling part, comprising:
a steam inlet on the handling part,
at least one steam outlet, and
a pipe connecting the steam inlet and the at least one steam outlet, the pipe comprising an adjustable temperature heating unit on the pipe; and
(d) a steam pipe which connects the steam inlet on the handling part with the low temperature steam outlet of the atomizing chamber, wherein the water in the water tank is caused to form a low temperature vapor by the atomization device, wherein the temperature of a low temperature vapor is increased by the heating unit on the handling part, and wherein the temperature of the vapor is adjusted by adjusting the heating unit.

In some embodiments, in the steam forming device of above embodiments, the output part is a handling part, the handling part comprising a head and a handle in a single body, the head comprising a plurality of massage rollers which are paratactically set on the head, wherein the handling part comprises a plurality of steam outlets which are respectively set between the corresponding massage rollers, wherein the steam inlet on the handling part is set on the end of the handle; and wherein the heating element is set inside the handle, the heating element comprising
a metal pipe tie-in comprising two ends, the two ends being connected with the steam pipe,
a PTC heating element set on the outside wall of the metal pipe tie-in, and
a thermostat which is connected with the PTC heating element.

In some embodiments, in the steam forming device of above embodiments, the atomizing chamber is located on the lower side of the water tank, the atomizing chamber being connected with outside atmosphere, wherein the water tank is sealed, wherein there is a water inlet valve between the water tank and the atomizing chamber, the water inlet valve including a cylinder valve body which is extending to the atomizing chamber where the inside of the valve body comprises a channel which connects the water tank with the atomizing chamber, and where the lower end of the valve body comprises a void, wherein the atomizing chamber is connected with steam outlet by a steam channel, the position of the inlet of the steam channel being higher than the void of the water inlet valve, wherein on the outside of the impeller there is a wind guiding shell, the wind guiding shell comprising a wind blowing mouth which is connected with the atomizing chamber and is near the inlet of the steam channel In some embodiments, in the steam forming device of above embodiments, the output part is a massage belt, on the inside surface of which there are several massage protruding points and a plurality of steam outlets which are respectively set between the corresponding massage protruding points, wherein the heating unit is set on outside surface of the massage belt, the heating unit comprising:
a metal pipe tie-in, the two ends of which are connected with the steam pipe,
a PTC heating element which is set on the outside wall of the metal pipe tie-in, and
a thermostat which is connected with the PTC heating element.

In some embodiments, in the steam forming device of above embodiments, the atomization device and the water tank are a single body structure which is connected with the output part by steam pipe.

In some embodiments, in the steam forming device of above embodiments, the atomizing chamber is located on the lower side of the water tank, the atomizing chamber being connected with outside atmosphere, wherein the water tank is sealed, wherein there is a water inlet valve between the water tank and the atomizing chamber, the water inlet valve including a cylinder valve body which is extending to the atomizing chamber where the inside of the valve body comprises a channel which connects the water tank with the atomizing chamber, and where the lower end of the valve body comprises a void, wherein the atomizing chamber is connected with steam outlet by a steam channel, the position of the inlet of the steam channel being higher than the void of the water inlet valve, wherein on the outside of the impeller there is a wind guiding shell, the wind guiding shell comprising a wind blowing mouth which is connected with the atomizing chamber and is near the inlet of the steam channel The length of application of the stream of hot vapor to a particular acupoint and/or a set of acupoints (period of application) can vary. Generally, the period of application is from about 1 minute to about 1 hour. In some embodiments, the period of application is from about 2 minutes to about 1 hr, about 3 minutes to about 1 hr, about 4 minutes to about 1 hr, about 5 minutes to about 1 hr, about 6 minutes to about 1 hr, about 7 minutes to about 1 hr, about 8 minutes to about 1 hr, about 9 minutes to about 1 hr, about 10 minutes to about 1 hr, about 15 minutes to about 1 hr, or about 30 minutes to about 1 hr. In some embodiments, the period of application is from about 1 minute to: about 5 minutes, about 10 minutes, about 15 minutes, about 30 minutes, or about 45 minutes. In some other embodiments, the period of application is from about 2 minutes to: about 5 minutes, about 10 minutes, about 15 minutes, about 30 minutes, about 45 minutes, or about 1 hr. In some other embodiments, the period of application is from about 5 minutes to: about 10 minutes, about 15 minutes, about 30 minutes, about 45 minutes, or about 1 hr. In some other embodiments, the period of application is from about 10 minutes to: about 15 minutes, about 30 minutes, about 45 minutes, or about 1 hr. In some other embodiments, the period of application is from about 15 minutes to: about 30 minutes, about 45 minutes, or about 1 hr. In some other embodiments, the period of application is from about 30 minutes to about 45 minutes or about 1 hr. In some other embodiments, the period of application is from about 45 minutes to about 1 hr.

The course of treatment can vary. Generally, the course of treatment can last about 1 month to about 10 years, about 3 months to about 10 years, about 6 months to about 10 years, about 1 year to about 10 years, about 2 years to about 10 years, about 3 years to about 10 years, about 4 years to about 10 years, about 5 years to about 10 years. Examples of course of treatment can last, e.g., 3 months, 6 months, 9 months, 1 year, 2 years, 3 years, 4 years, 5 years, 6 years, 7 years, 8 years, 9 years, 10 years or longer.

BRIEF DESCRIPTION OF THE DRAWINGS

FIGS. 2A-2I show embodiments of acupuncture device of invention.

DESCRIPTION OF EXEMPLARY EMBODIMENTS OF THE INVENTION

Figure 1A:
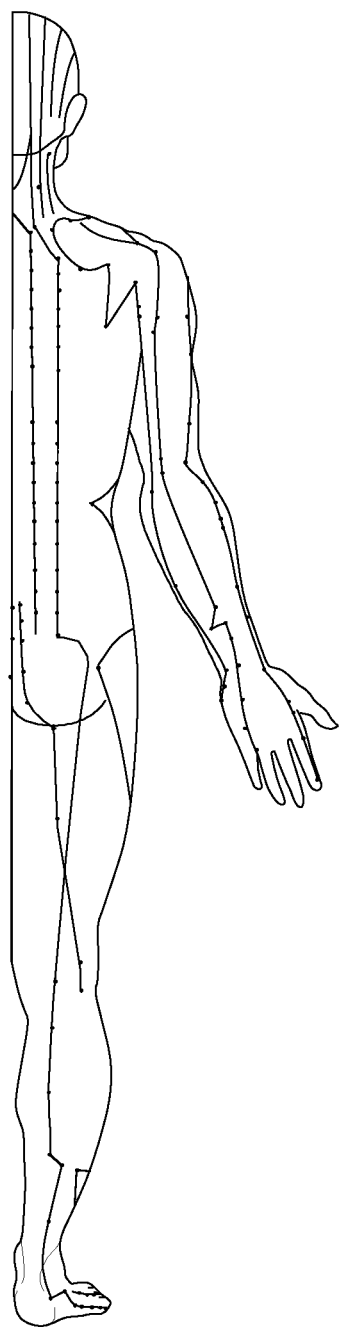
FIGS. 1A and 1B illustrate the acupoints in the back (A) and front (B) of a human body.

In one aspect, it is provided a method of providing treatment of a sleeping disorder. The method comprises applying a stream of low temperature vapor to a set of acupoints or an acupoint when one feels hungry for a period of time in a course of treatment, thereby improving condition of a sleeping disorder or ameliorating symptoms of a sleeping disorder.

In some embodiments, the sleeping disorder is insomnia. Acupoints for a sleeping disorder include fengchi, yongquan, and shimian.

As used herein, the term condition of a sleeping disorder refers to any physical, biological or biochemical condition of a sleeping disorder patient as compared with a normal human being, which conditions are generally known in the art. In some embodiments, the condition of a sleeping disorder can be used interchangeably with the term symptom.

As used herein, the term "low temperature vapor" refers to a hot stream of steam having a temperature above the body temperature (e.g., 37° C.) that will not cause any injury to skin or otherwise damage the skin. In some embodiments, the term "low temperature vapor" refers to a hot stream of steam having a temperature at about 50° C. or below, e.g., from about 38° C. to about 50° C., from about 40° C. to about 50° C., from about 40° C. to about 45° C., or from about 45° C. to about 50° C. Examples of the temperature of a hot stream of steam can be, e.g., about 40° C., about 42° C., about 45° C., about 47° C., about 50° C., or in some embodiments about 55° C.

In some embodiments, the low temperature vapor steam is generated by a steam forming device described in U.S. Pat. No. 7,634,176, the teaching of which is incorporated herein in its entirety by reference. An example of the device described in U.S. Pat. No. 7,634,176 is shown in FIGS. 2A to 2I.

In some embodiments, the steam forming device comprises
(a) an atomization device comprising:
an atomizing chamber comprising a low temperature vapor outlet,
an atomizer which is located in the atomizing chamber to make the water become a low temperature vapor, and
an impeller driving the low temperature vapor of the atomizing chamber into the outlet;
(b) a high temperature steam forming device for producing high temperature steam comprising a high temperature steam outlet;
(c) a steam outlet pipe, comprising:
two steam intakes which are respectively connected with the low temperature vapor outlet of the atomizing chamber and high temperature steam outlet of the high temperature steam forming device, and
a mixing steam outlet; and
(d) a water tank for supplying needed water for the atomization device and the high temperature steam forming device,
wherein a stream of water from the water tank passes through the atomizing device to generate a low temperature vapor,
wherein another stream of water from the water tank passes through the steam forming device to generate a high temperature steam,
wherein the high temperature steam and the low temperature vapor are mixed by the steam outlet pipe, and
wherein the composition of the mixed steam is adjusted by adjusting the proportions of the high temperature steam and the low temperature vapor.

In some embodiments, in the steam forming device of the above embodiments, the water tank comprises:
a main water tank located on the upper side,
an assistant water tank located on the lower side,
a water inlet valve between the main water tank and the assistant water tank, and
a wind guiding shell comprising a wind blowing mouth,
wherein the atomizing chamber is set on one side of and connected with the assistant;
wherein the low temperature steam outlet is set on the top of the atomizing chamber;
wherein the wind guiding shell is set outside of the impeller, the wind blowing mouth of the wind guiding shell facing the bottom of the low temperature steam outlet; and
wherein the water inlet pipe of the high temperature steam forming device is connected with the bottom of the assistant water tank where a water volume adjusting valve being set on the connecting area and the water volume adjusting valve comprises a knob which is adjustable outside.

In some embodiments, in the steam forming device of the above embodiments, the water inlet valve includes a cylinder valve body which is protruding into the assistant water tank from the bottom of the main water tank, wherein the bottom edge of the valve comprises a void, the position of the void being lower than the position of the wind blowing mouth;

wherein the valve comprises a valve hole in the middle of the valve body;

wherein in the valve hole there is a valve stopper which tightly fills the valve hole from the bottom to the top;

wherein the stopper comprises an up-extending valve stick on the top of the stopper, the valve stick comprising a spring causing the valve stick to move up to tightly fill the valve hole; and wherein the main water tank comprises a water inlet on the top of the main water tank, the water inlet comprises a knob cover, the bottom of which comprises a connecting rod which extends into the main water tank and is capable of pushing the valve stick downward so as to cause the valve stopper to pull away from the valve hole.

In some embodiments, in the steam forming device of the above embodiments, wherein the mixing steam outlet of the steam guiding output pipe is connected with a hollow ring by a steam pipe, wherein on the bottom of the hollow ring there are many steam ejecting holes along the circumference, and wherein the hollow ring is set on a rack.

In some embodiments, in the steam forming device of the above embodiments, wherein there is a heating unit located on the jointing position of the steam pipe and the hollow ring, wherein the heating unit comprises:
a metal pipe tie-in comprising two ends, the two ends being connected with the steam pipe,
a PTC heating element set on the outside wall of the metal pipe tie-in, and
a thermostat which is connected with the PTC heating element.

In some further embodiments of the method, the steam forming device is equipped to provide steam of adjustable temperature, the device comprises:
(a) an atomization device comprising:
an atomizing chamber,
an atomizer located in the atomizing chamber for causing water to become to low temperature vapor, and
an impeller for driving the low temperature vapor in the atomizing chamber to flow toward outlet;
(b) a water tank for supplying water to the atomization device;
(c) an output part comprising a handling part, comprising:
a steam inlet on the handling part,
at least one steam outlet, and
a pipe connecting the steam inlet and the at least one steam outlet, the pipe comprising an adjustable temperature heating unit on the pipe; and
(d) a steam pipe which connects the steam inlet on the handling part with the low temperature steam outlet of the atomizing chamber, wherein the water in the water tank is caused to form a low temperature vapor by the atomization device, wherein the temperature of a low temperature vapor is increased by the heating unit on the handling part, and wherein the temperature of the vapor is adjusted by adjusting the heating unit.

In some embodiments, in the steam forming device of above embodiments, the output part is a handling part, the handling part comprising a head and a handle in a single body, the head comprising a plurality of massage rollers which are paratactically set on the head, wherein the handling part comprises a plurality of steam outlets which are respectively set between the corresponding massage rollers, wherein the steam inlet on the handling part is set on the end of the handle; and wherein the heating element is set inside the handle, the heating element comprising
a metal pipe tie-in comprising two ends, the two ends being connected with the steam pipe,
a PTC heating element set on the outside wall of the metal pipe tie-in, and
a thermostat which is connected with the PTC heating element.

In some embodiments, in the steam forming device of above embodiments, the atomizing chamber is located on the lower side of the water tank, the atomizing chamber being connected with outside atmosphere, wherein the water tank is sealed, wherein there is a water inlet valve between the water tank and the atomizing chamber, the water inlet valve including a cylinder valve body which is extending to the atomizing chamber where the inside of the valve body comprises a channel which connects the water tank with the atomizing chamber, and where the lower end of the valve body comprises a void, wherein the atomizing chamber is connected with steam outlet by a steam channel, the position of the inlet of the steam channel being higher than the void of the water inlet valve, wherein on the outside of the impeller there is a wind guiding shell, the wind guiding shell comprising a wind blowing mouth which is connected with the atomizing chamber and is near the inlet of the steam channel In some embodiments, in the steam forming device of above embodiments, the output part is a massage belt, on the inside surface of which there are several massage protruding points and a plurality of steam outlets which are respectively set between the corresponding massage protruding points, wherein the heating unit is set on outside surface of the massage belt, the heating unit comprising:
a metal pipe tie-in, the two ends of which are connected with the steam pipe,
a PTC heating element which is set on the outside wall of the metal pipe tie-in, and
a thermostat which is connected with the PTC heating element.

In some embodiments, in the steam forming device of above embodiments, the atomization device and the water tank are a single body structure which is connected with the output part by steam pipe.

In some embodiments, in the steam forming device of above embodiments, the atomizing chamber is located on the lower side of the water tank, the atomizing chamber being connected with outside atmosphere, wherein the water tank is sealed, wherein there is a water inlet valve between the water tank and the atomizing chamber, the water inlet valve including a cylinder valve body which is extending to the atomizing chamber where the inside of the valve body comprises a channel which connects the water tank with the atomizing chamber, and where the lower end of the valve body comprises a void, wherein the atomizing chamber is connected with steam outlet by a steam channel, the position of the inlet of the steam channel being higher than the void of the water inlet valve, wherein on the outside of the impeller there is a wind guiding shell, the wind guiding shell comprising a wind blowing mouth which is connected with the atomizing chamber and is near the inlet of the steam channel The length of application of the stream of hot vapor to a particular acupoint and/or a set of acupoints (period of application) can vary. Generally, the period of application is from about 1 minute to about 1 hour. In some embodiments, the period of application is from about 2 minutes to about 1 hr, about 3 minutes to about 1 hr, about 4 minutes to about 1 hr, about 5 minutes to about 1 hr, about 6 minutes to about 1 hr, about 7 minutes to about 1 hr, about 8 minutes to about 1 hr, about 9 minutes to about 1 hr, about 10 minutes to about 1 hr, about 15 minutes to about 1 hr, or about 30 minutes to about 1 hr. In some embodiments, the period of application is from about 1 minute to: about 5 minutes, about 10 minutes, about 15 minutes, about 30 minutes, or about 45 minutes. In some other embodiments, the period of application is from about 2 minutes to: about 5 minutes, about 10 minutes, about 15 minutes, about 30 minutes, about 45 minutes, or about 1 hr. In some other embodiments, the period of application is from about 5 minutes to: about 10 minutes, about 15 minutes, about 30 minutes, about 45 minutes, or about 1 hr. In some other embodiments, the period of application is from about 10 minutes to: about 15 minutes, about 30 minutes, about 45 minutes, or about 1 hr. In some other embodiments, the period of application is from about 15 minutes to: about 30 minutes, about 45 minutes, or about 1 hr. In some other embodiments, the period of application is from about 30 minutes to about 45 minutes or about 1 hr. In some other embodiments, the period of application is from about 45 minutes to about 1 hr.

The course of treatment can vary. Generally, the course of treatment can last about 1 month to about 10 years, about 3 months to about 10 years, about 6 months to about 10 years, about 1 year to about 10 years, about 2 years to about 10 years, about 3 years to about 10 years, about 4 years to about 10 years, about 5 years to about 10 years. Examples of course of treatment can last, e.g., 3 months, 6 months, 9 months, 1 year, 2 years, 3 years, 4 years, 5 years, 6 years, 7 years, 8 years, 9 years, 10 years or longer.

Acupuncture and Acupoints

Acupuncture, practiced for several thousand years in China (Veith I. The yellow emperor's classic of internal medicine. Williams & Wilkins: Baltimore; 1949. pp 58-76.), is increasingly used worldwide in the treatment of many disorders. An accumulating body of evidence summarized in a NIH Consensus Statement on Acupuncture (NIH Consensus Development Panel. Acupuncture. JAMA 1998; 280: 1518-1524) confirms that acupuncture treatment has beneficial effects for conditions ranging from postoperative dental pain to chemotherapy-associated emesis. It is also effective as an adjunctive modality for joint and muscle pain, addictions, and asthma, for example.

Meridians and Acupoints

Figure 1B:
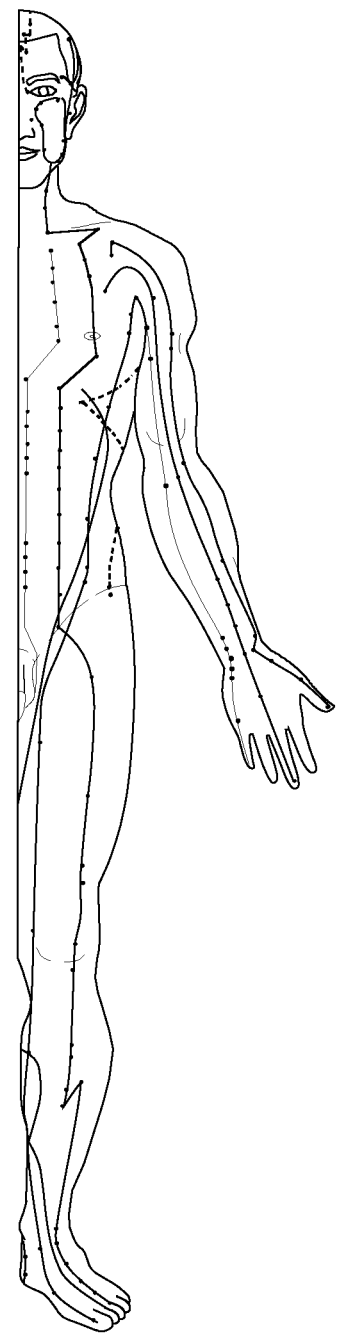

In Traditional Chinese Medicine (TCM), life force or 'Qi' ('chee') is thought to circulate within energy pathways or 'meridians' longitudinally throughout the body. There are 14 major meridians, corresponding (loosely) to the Western definition of 'organs.' Acupoints are specific locations on the body considered to be connected to these energy meridians (FIGS. 1A and 1B) (NIH Consensus Development Panel. Acupuncture. JAMA 1998; 280: 1518-1524; Vickers A, Zollman C. ABC of complementary medicine: acupuncture. BMJ 1999; 319: 973-976; and Mitchell ER. Fighting drug abuse with acupuncture: the treatment that works. Pacific View Press: Berkeley, Calif.; 1995). During illness Qi is thought to be out of balance, and stimulation of acupoints corrects this imbalance. Theoretically, an 'excess' or 'deficiency' of Qi can be 'normalized' by the specific manner of point stimulation.

Using this paradigm, obesity and/or excess appetite has been conceptualized in a variety of ways, such as 'heat' in the stomach and intestine (Li J. Clinical experience in acupuncture treatment of obesity. J Tradit Chin Med 1999, 19: 48-51), a deficiency of Qi in the spleen and stomach (Id.; Stux G, Pomeranz B. Acupuncture: textbook and atlas. Springer-Verlag: Berlin; 1987), or a deficiency of primary Qi (Li J. Clinical experience in acupuncture treatment of obesity. J Tradit Chin Med 1999, 19: 48-51). Based on these beliefs about the causes of obesity, a variety of acupoints are targeted in the treatment of obesity, including: Neiguan (P 6), Fenglong (St 40), Liangmen (St 21), Guanyuan (R 4), Zusanli (St 36), Tianshu (St 25), Quchi (LI 11), where P refers to a lung point, St to stomach, R to kidney, and LI to large intestine (Sun Q, Xu Y. A survey of the treatment of obesity by traditional Chinese medicine. J Tradit Chin Med 1993; 13: 124-128).

In terms of traditional medicine, it is believed that acupuncture works to alter central nervous system neurotransmitter levels by stimulating peripheral nerves at acupoints. These stimulated nerves then carry the signals centrally (Stux G, Pomeranz B. Basics of acupuncture, 4th edn. Springer-Verlag: Berlin; 1998; Mann F. Acupuncture: cure of many diseases. Butterworth-Heinemann Ltd.: Oxford; 1992), shown in FIG. 3, including to the spinal cord, pituitary, and midbrain. Activated centers can then release neurochemicals: endorphins, monoamines, and cortisol (Stux G, Pomeranz B. Basics of acupuncture, 4th edn. Springer-Verlag: Berlin; 1998).

Acupoint Stimulation

A large number of acupoints (365 points have been identified in Chinese acupuncture maps) (FIGS. 1A and 1B) show concentrations of peripheral nerve junctions, referred to as 'trigger points (Vickers A, Zollman C. ABC of complementary medicine: acupuncture. BMJ 1999; 319: 973-976). A variety of methods are used to stimulate acupoints (NIH Consensus Development Panel. Acupuncture. JAMA 1998; 280: 1518-1524; Stux G, Pomeranz B. Basics of acupuncture, 4th edn. Springer-Verlag: Berlin; 1998; Lao L. Acupuncture technique and devices. J Ahern Complem Med 1996; 2: 23-25). These include:

1. Needling or 'traditional acupuncture', in which fine stainless-steel needles are inserted through the skin to various depths, kept in place for varying lengths of time and/or further stimulated manually or electrically ('electroacupuncture').
2. Press needles or 'staplepuncture' in which short acupuncture needles are taped into place for extended periods with pressure being applied on a regular basis.
3. 'Acupressure' in which beads are massaged or pressed at specific locations.
4. 'Moxibustion' involving the application of heat, by burning small grain-sized pellets of combustible material on or near the acupoints.
5. 'Cupping' or using cups of various materials to create 'negative pressure' or a vacuum on the skin surface for increased blood circulation and point stimulation.
6. Transcutaneous electrical nerve stimulation ('TENS') which involves applying electrode pads to the skin surface which transmit a mild current into the acupoint.

See, e.g., J M Lacey, et al., Acupuncture for the treatment of obesity: a review of the evidence, International Journal of Obesity (2003) 27, 419-427. doi:10.1038/sj.ijo.0802254. The teachings in the references in the preceding paragraphs are incorporated herein in their entirety by reference.

As used herein, the term "vapor acupuncture device" is used interchangeably with the term "hot vapor acupuncture device" or "thermal acupuncture device" or "steam acupuncture device". In some embodiments, these terms are used interchangeably with the term "steam forming device."

Acupoints for Sleeping Disorders

In some embodiments, the sleeping disorder is insomnia. Acupoints for treating a sleeping disorder using a device of the present invention include fengchi, yongquan, and shimian. These acupoints are fully described in the acupoints diagram generally available in the art. Please refer to FIGS. 1A and 1B to identify any of these acupoints. In traditional Chinese medicine (TCM), the meridians system is profound and well known in acupoint massage, health care, treatment and beauty maintenance. In particular, the term "meridians" refers to running blood, the channel of connecting the body surface, organs and the other parts of body. The term "acupoints" refers to the special position on the meridians, and the special fortress of blood transport in and out of the organs. Acupoints Massage is used for regulating the meridians, improving local blood, rebalancing yin and yang, regulating and rebalancing the organs, thus reaching the purpose of health care and auxiliary treatment of chronic diseases. However, it is difficult to accurately grasp the meridians, acupuncture points and apply the specific location for most ordinary people. Using the Aqu-Puncture, it gets an area stimulation, micro-vibration action, temperature and steam heat, and the role of negative ions too. It turns the profession to common people (non-practitioners), so everyone can enjoy "Green Health."

For a particular type of a sleeping disorder, the acupoints include the above described set of acupoints and further, additional acupoints.

Acupuncture has been shown to be effective for treating or ameliorating sleeping disorders such as insomnia (see, e.g., Cheuk D K L, Yeung J, Chung K, Wong V. Acupuncture for insomnia. Cochrane Database of Systematic Reviews 2007, Issue 3. Art. No.: CD005472. DOI: 10.1002/14651858.CD005472.pub2); and Cao H, Pan X, Li H, Liu J., Acupuncture for treatment of insomnia: a systematic review of randomized controlled trials, in J Ahern Complement Med. 2009 November; 15(11):1171-86).

Steam Forming Device

The steam forming device useful for the present invention can have design of any type. In some embodiments of the present invention, the steam forming device is shown in FIGS. 2A-2D. The following is discussed in reference to FIG. 2A to FIG. 2D.

The embodiment supplies a hair treatment elixir machine which adopts the invention device for forming adjustable temperature vapor, referring to FIG. 2(1), the hair treatment elixir machine including a base 1, an up-extending supporting stick 12 which is vertical to and set on the base 1, a connecting base 14 which is set on the top of the supporting stick 12, a connector 13 which is engaged with the connecting base 14 by a screw 15 which is located on vertical direction, a steam ejecting ring 3 which is set on the connector 13, the device 2 for forming vapor which is located on the middle of the supporting stick 12. On the top of the steam forming device 2 there is a water inlet 850, on the water inlet 850 there a knob cover 85, the steam forming device 2 is connected with the said steam ejecting ring 3 by a steam pipe 31. The steam forming device 2 also comprises a knob 83 to regulate the temperature of the output steam.

Figure 2A:
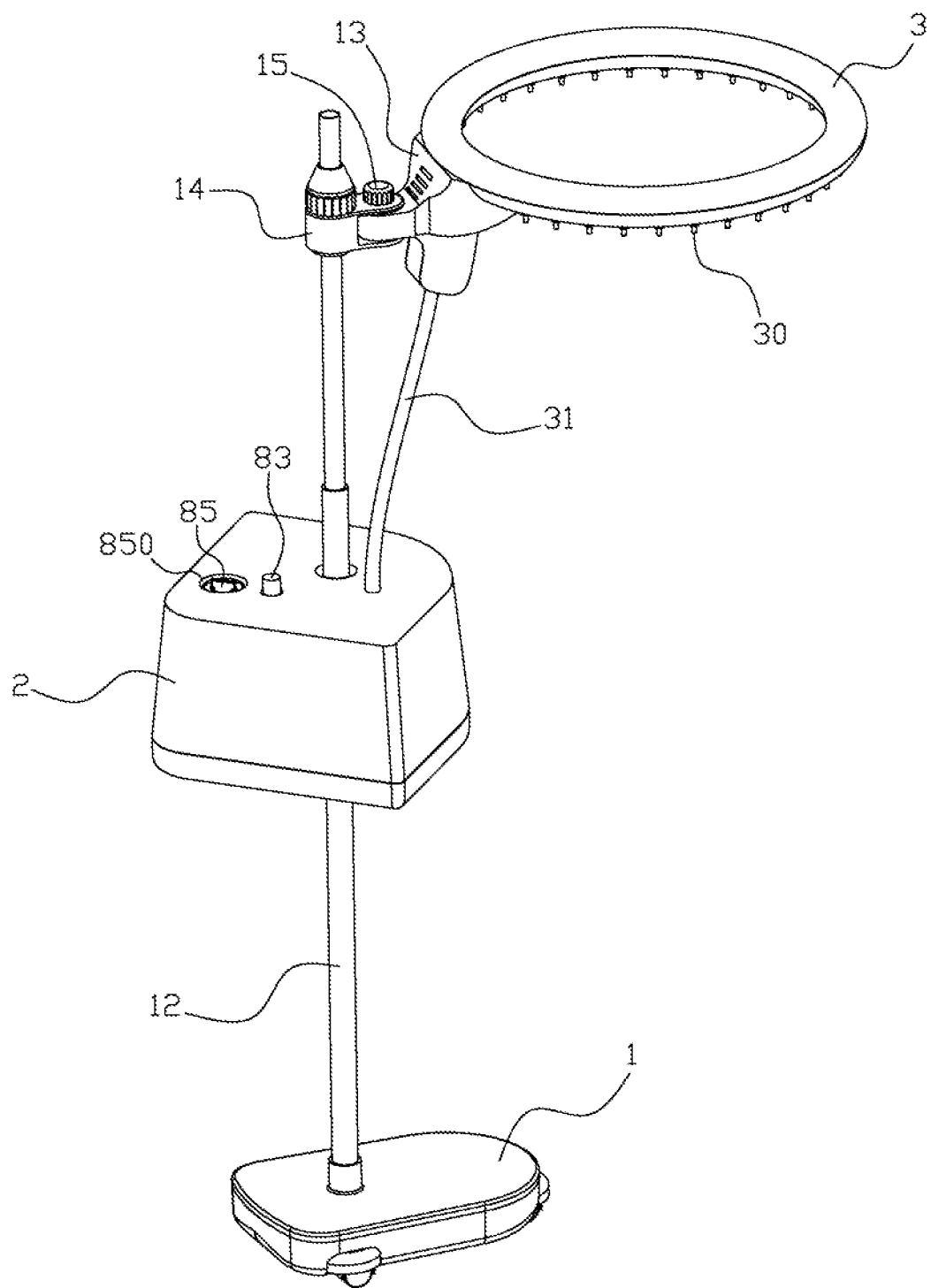
Figure 2B:
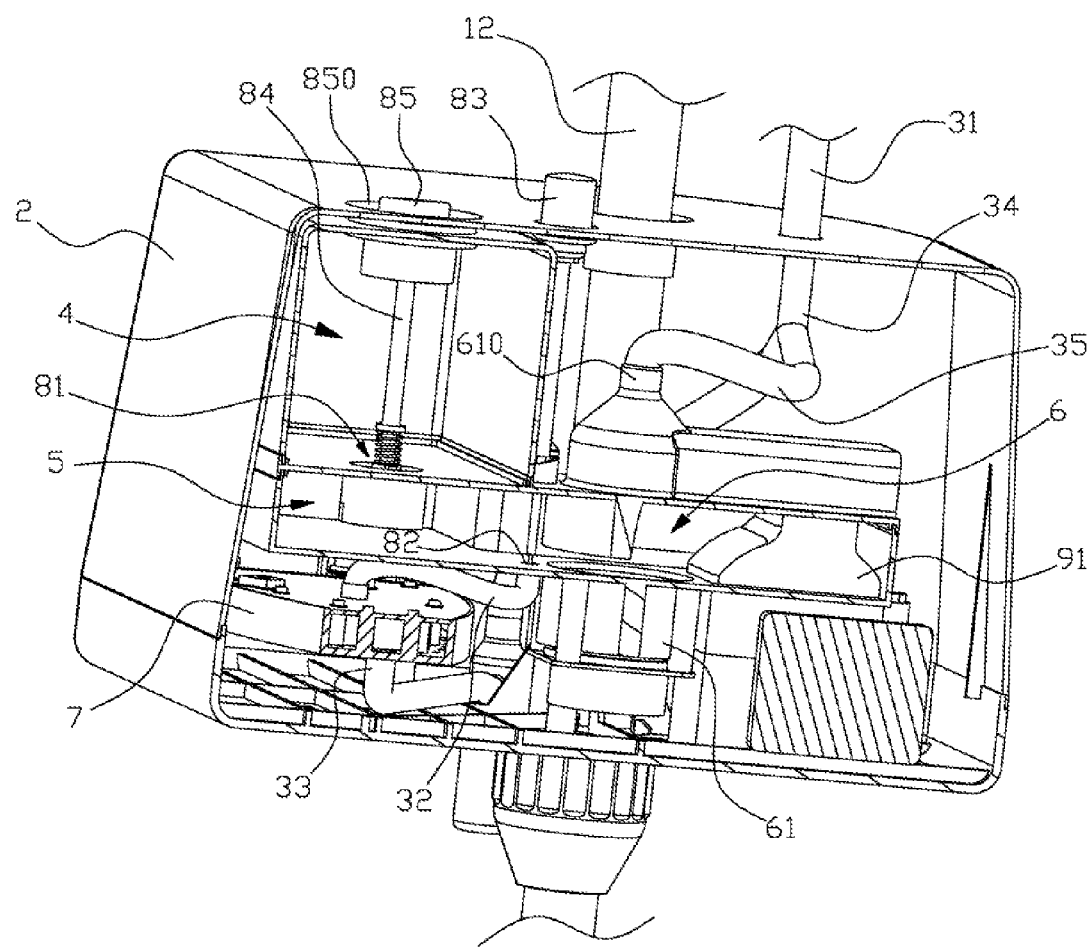
Figure 2C:
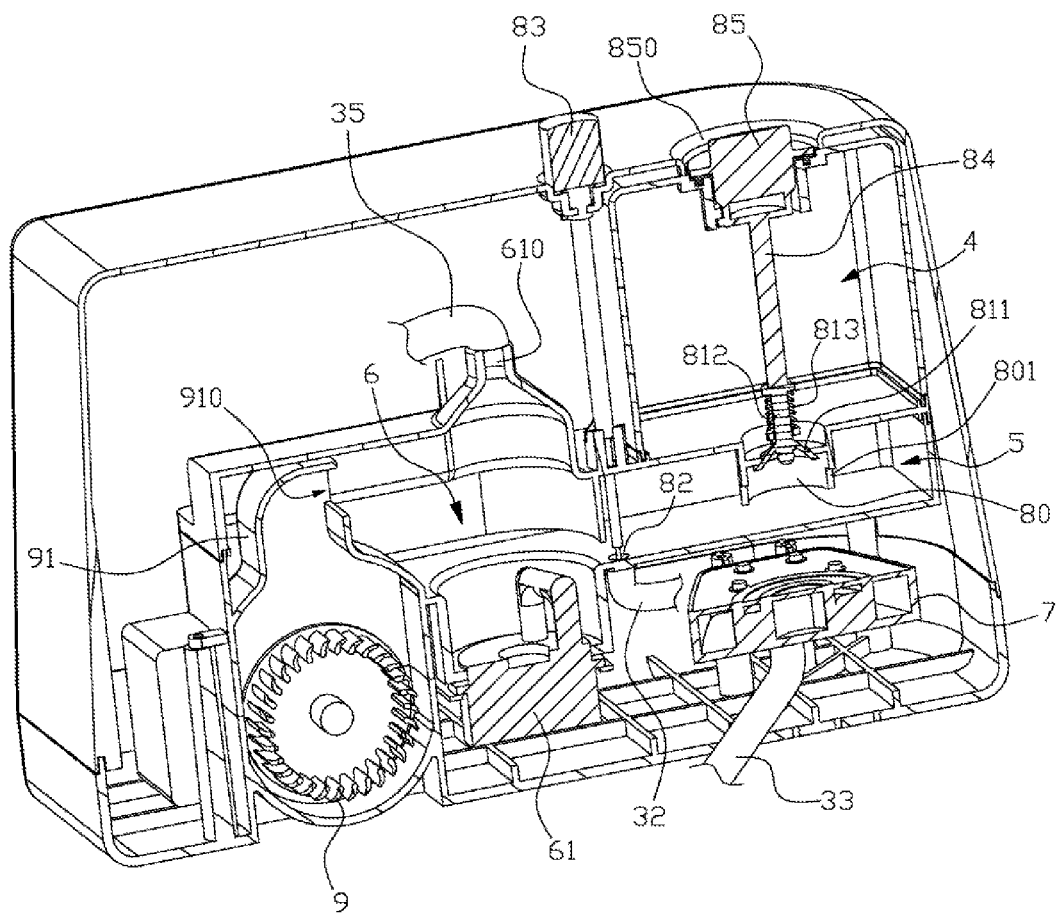

Referring to FIG. 2B and FIG. 2C, the steam forming device 2 is sectional cut from two different positions to show its inside structure. The steam forming device 2 includes a main water tank 4, on the lower side of the main water tank 4 there is a assistant water tank 5, between the main water tank 4 and assistant water tank 5 there is a water inlet valve 81 which can control the water of main water tank 4 flowing into assistant water tank 5 and can also control the water level of the assistant water tank 5. There is a atomizing chamber 6 on one side of the assistant water tank 5 there is a atomizing chamber 6 which is connected with the assistant water tank 5, the upper side of the atomizing chamber 6 forms a low temperature steam outlet 610 which's inside wall is cone-shaped. In the atomizing chamber 6 there is a atomizer 61 which can make the water of the atomizing chamber 6 become to the low temperature vapor. On one side of the atomizing chamber 6 there is a impeller 9 which is driven by a motor which is not shown in the drawing. Outside of the impeller 9 there is a wind guiding shell 91 comprising a wind blowing mouth 910 facing the bottom of the low temperature steam outlet 610.

On the lower side of the assistant water tank 5 there is a high temperature steam formed device 7 which already adopted the steam forming device which is commonly used in electric steam iron, so its structure is not explained in detail here. The water inlet pipe 32 of the high temperature steam forming device 7 is connected with the bottom of the assistant water tank 5, on the jointing area there is a water volume adjusting valve 82 which comprises a knob 83 which is adjustable outside. The water volume adjusting valve 82 can adopt any structure of water volume adjusting valve of existing technology as long as it can adjust the water passing speed. So by regulating the knob 83, one can adjust the water volume which enters the high temperature steam forming device 7, equal to adjusting the forming volume of the high temperature steam.

Referring to FIG. 2C, the water inlet valve 81 includes a cylinder valve body 80 which is protruding into the assistant water tank 5 from the bottom of the main water tank 4. The bottom edge of the valve 80 comprises a void 801, the position of the void 801 is lower than the position of the wind blowing mouth 910; the valve 80 comprises a valve hole in the middle of the valve body. In the valve hole there is a valve stopper 811 which tightly fills the valve hole from the bottom to the top. The stopper 811 comprises an up-extending valve stick 812 on the top of the stopper, the valve stick 812 comprising a spring 813 causing the valve stick 812 to move up to tightly fill the valve hole; the main water tank 4 comprise a water inlet 850 on the top of the main water tank, the water inlet 850 comprises a knob cover 85, the bottom of which comprises a connecting rod 84 which extends into the main water tank 4 and is capable of pushing the valve stick 812 downward so as to cause the valve stopper 811 to pull away from the valve hole.

When opening the knob cover 85 to fill water to the main water tank 4 through water inlet 850, forced by the spring 813, the valve stopper 811 tightly fills the valve hole, keeping the water of the main water tank 4 from entering the assistant water tank 5. When the knob cover 85 is set on the water inlet 850 tightly, the main water tank 4 is a sealed space, while the assistant water tank 5 is connected with outside atmosphere, when the water level of the assistant water tank 5 is lower than the void 801 which is set on the bottom edge of the valve 80, the water of the main water tank 4 can flow into the assistant water tank 5 automatically through the valve hole in the middle of the valve 80, when the water level of the assistant water tank 5 rises and submerges the void 801, since the main water tank 4 is sealed, the inside forms minus pressure, the water of the main water tank 4 can't flow down to the assistant water tank 5.

Referring to FIG. 2B, the lower end of the steam pipe 31 is connected with the steam outlet pipe 34 which is located in the steam forming device 2, the steam outlet pipe 34 comprises two steam inlets which are respectively connected with the low temperature steam outlet 610 of the atomizing chamber 6 and the high temperature steam outlet pipe 33 of the high temperature steam forming device 7, a mixing steam outlet which is connected with steam outlet pipe 31.

Figure 2D:
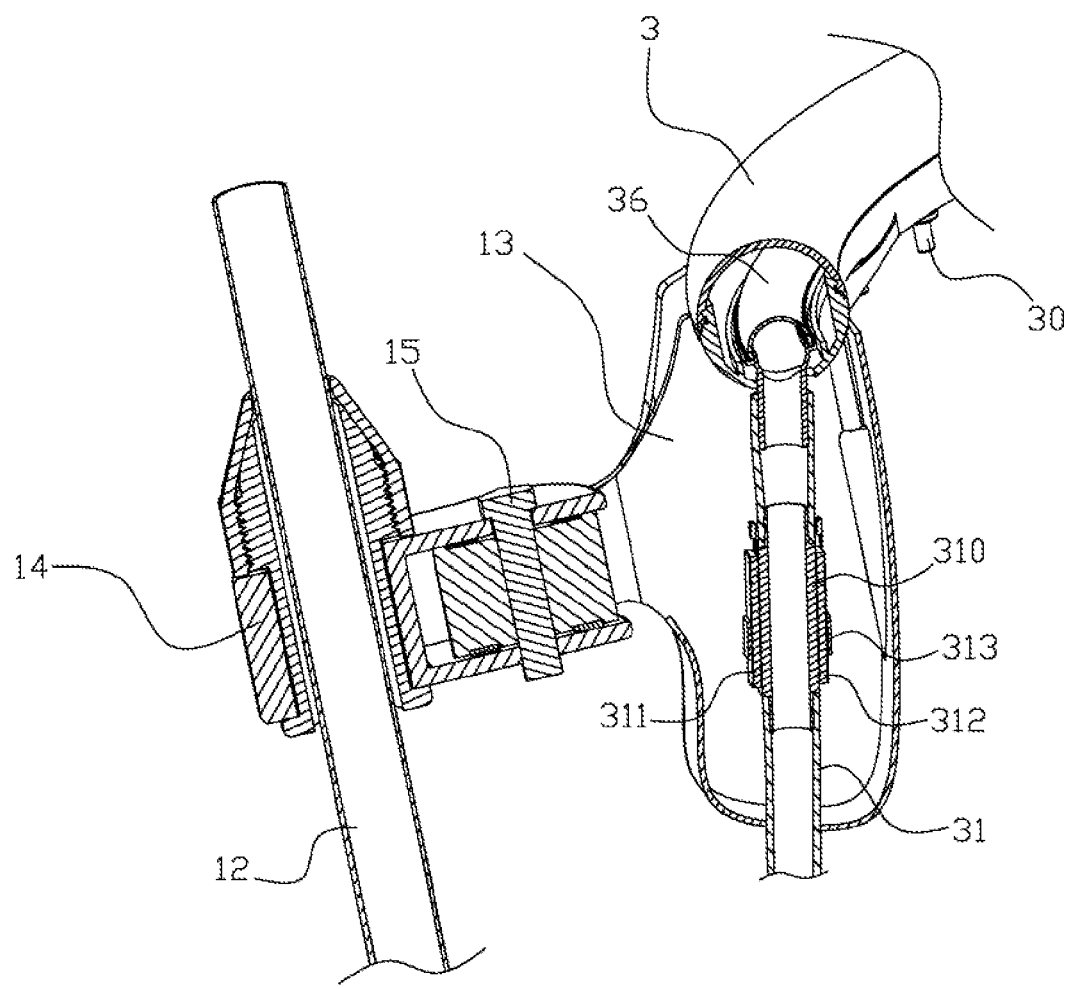

Referring to FIG. 2D, there is a hollow ring 36 in the steam ejecting ring 3, there are many steam ejecting holes 30 on the bottom of the hollow ring 36, each steam ejecting hole 30 extending down and going out of the steam ejecting ring 36, the steam pipe 31 is connected with the hollow ring 36. The jointing area of the steam pipe 31 and the hollow ring 36 comprise a heating unit. The heating unit comprises: a metal pipe tie-in 310 comprising two ends, the two ends being connected with the steam pipe 31, a PTC heating elements 311, 312 set on the outside wall of the metal pipe tie-in 310 and a thermostat which is connected with the PTC heating elements 311,312, the thermostat is the existing technology, not shown in FIG. 2D, the metal pipe tie-in 310 and the PTC heating elements 311,312 are located in the said connector 13 by a fixture 313.

Summarizing all the above, if the low temperature vapor formed in the atomizing chamber 6 is mixed with the high temperature steam formed by high temperature steam forming device 7, a vapor with a proper temperature will be generated which is to be applied in treating hair, and the composition of the mixed steam is adjusted by adjusting the proportions of the high temperature steam and the low temperature vapor.

Below is referred to FIG. 2E to FIG. 2I to explain the second embodiment of the present invention.

Figure 2E:
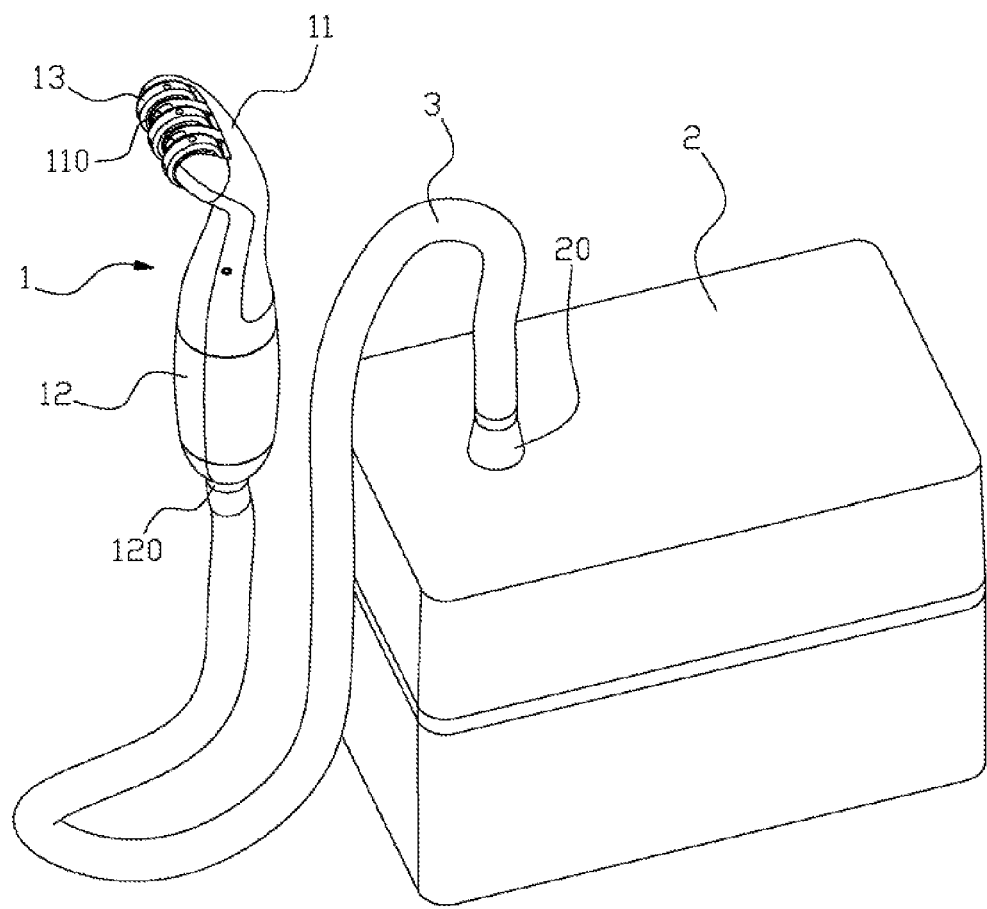

The embodiment is a kind of hand held device to care for the local skin by steam. Referring to FIG. 2E, the skin care device using steam comprises a handle 1 and a steam forming device 2. The handle 1 comprises a head 11 and a handle 12 in a single body, there are three massage rollers 13 set on the same axes paratactically on the head 11, there is a steam outlet 110 between the corresponding two massage rollers, and on the bottom of the handle 12, there is a steam inlet 120; the steam forming device 2 comprises a steam outlet 20 which is connected with the steam inlet 120 of the handle 1 by a steam pipe 3.

Referring to FIGS. 2F and 2G in the handle 1 there is a pipe 31 which connects the steam outlet 110 with the steam inlet 120. On pipe 31 there is a heating unit which heats the passing steam; the heating unit is located in the handle 11, comprising a metal pipe tie-in 4 comprising two ends, the two ends being connected with the steam pipe 31. The PTC heating element 41, 42 is set on the outside wall of the metal pipe tie-in 4, and a thermostat is connected with the PTC heating elements 41, 42. The thermostat is existing technology, not shown in the Figure.

Referring to FIG. 2I, the shell of the hand held part 1 comprises upper shell 101, upper rear cover 102, handle shell 103 and bottom cover 104 which are connected each other by wedges, upper shell 101, upper rear cover 102 form the said head 11, and the handle shell 103 and the bottom cover 104 form the handle 12. Inside of the head 11, there are two steam channels 311, 312 which are formed by the protruding ribs located in inside wall of the upper shell 101 and upper rear cover 102, the steam channels 311, 312 are connected between the steam pipe 31 and the two steam outlets 110, separating the steam pipe 31 to two branches, so as to make the steam of the steam pipe 31 ejecting from the two steam outlets 110. The metal pipe tie-in 4 and the PTC heating elements 41, 42 form the heating unit which is installed in the handle shell 103, its two ends being connected with the steam pipe 31 and the steam pipe 3 respectively.

There is a vibrator 14 in the head 11 of the hand held part 1 to increase the efficiency of the massage.

Figure 2H:
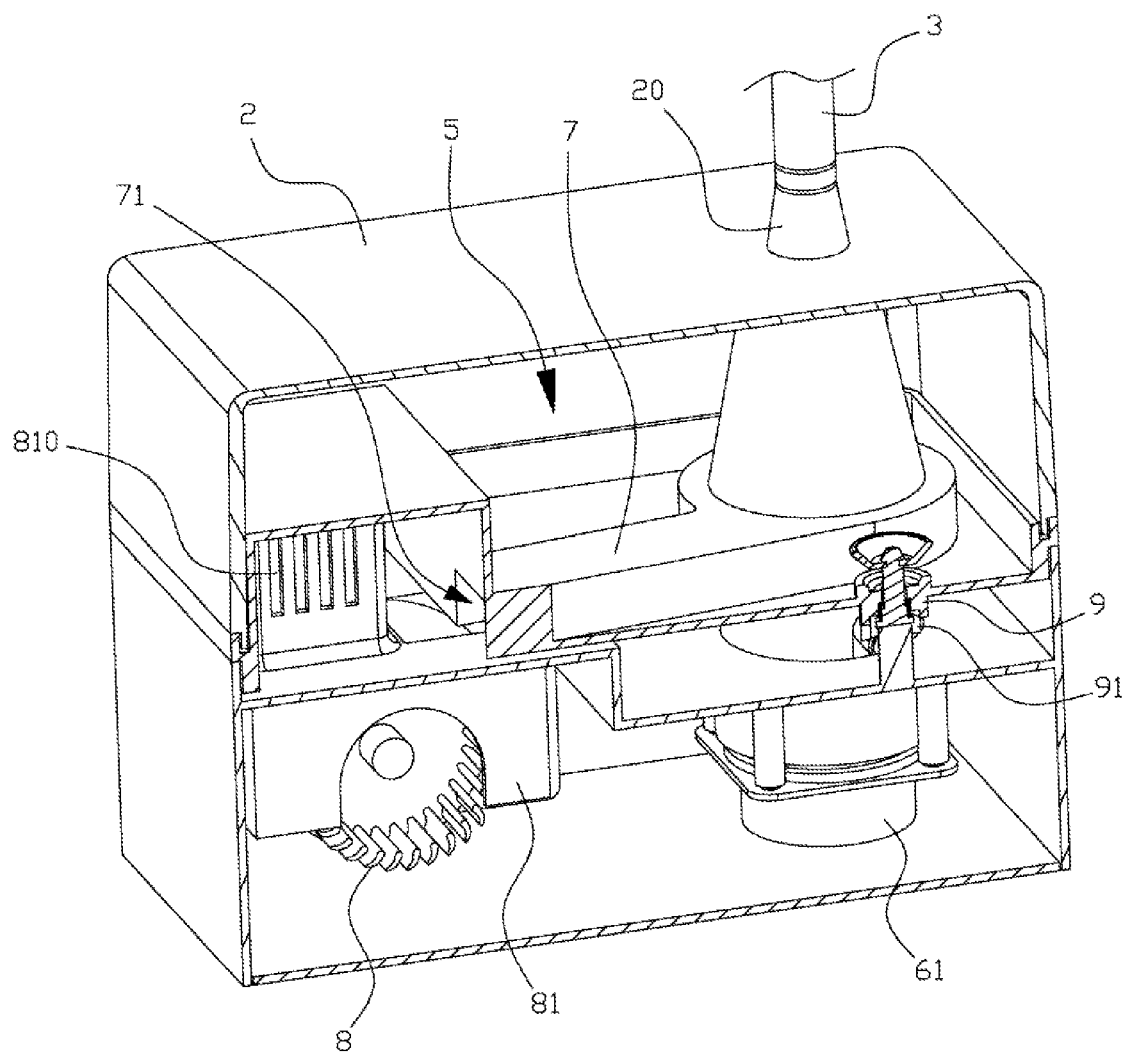
Figure 21:
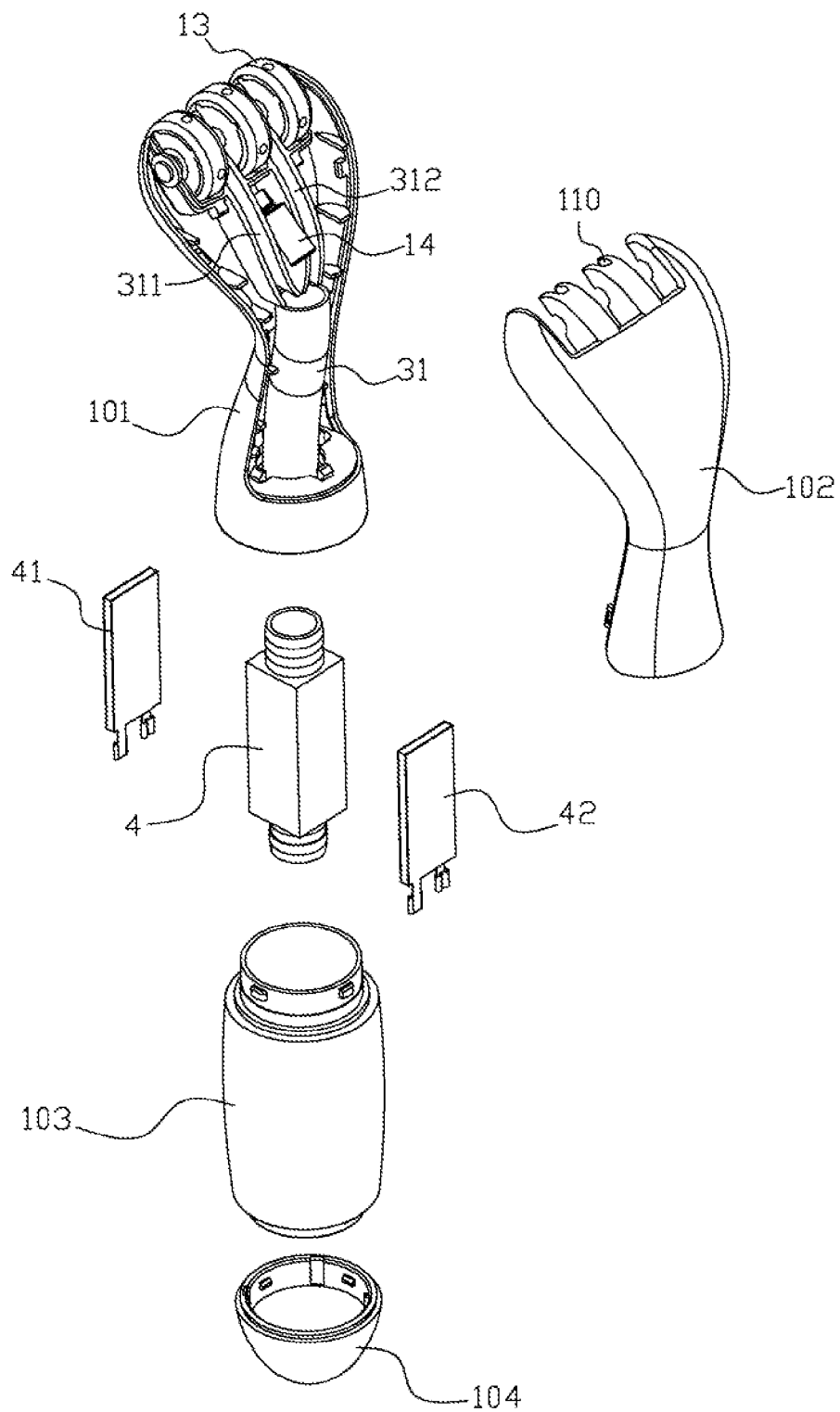
Figure 3:
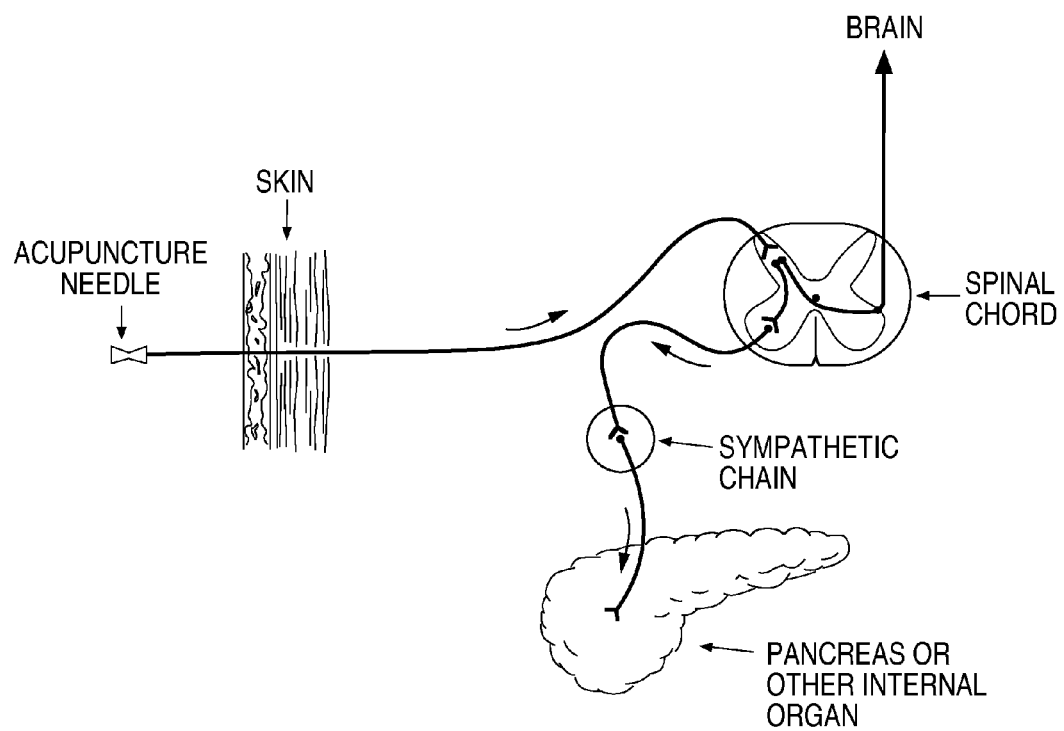
FIG. 3 shows simplified theoretical pathway of needle stimulation sending nerve impulses to brain and internal organs.

Referring to FIGS. 2F, 2G and 2H, these figures are two sectional plane drawings of the steam forming device 2, according to the position of the steam outlet 20 shown in the drawing, one can easily conclude the position and angle of the sectional cutting. The steam forming device 2 comprises the water tank 5, atomizing chamber 6, the water inlet valve 9 set between the water tank 5 and atomizing chamber 6, the atomizer 61 set in the atomizing chamber 6, the steam outlet 20 which is connected with the atomizing chamber 6 by a steam channel 7, the impellor 8 which drives the steam of the atomizing chamber 6 flowing into the steam outlet 20, and a motor which drives the impellor 8, the motor not shown in the drawing, as long as its output shaft is connected with the rotating shaft of the impellor 8. The inside wall of the steam outlet 20 is a cone surface which's smaller end is connected with the said steam pipe 3, the structure is good for the low temperature steam going to the steam pipe 3.

Atomizing chamber 6 is located on the lower side of the water tank 5. The atomizing chamber 6 is connected with outside atmosphere. The water tank 5 is sealed. The said water inlet valve 9, which is set between the water tank 5, and atomizing chamber 6 comprises a valve extending down to the atomizing chamber, the valve comprises a channel which connects the water tank with the atomizing chamber, and there is a void 91 on opening area of lower side of the channel; the inlet 71 position of the steam channel 7 is higher than the void 91, the impellor 8 is located on the lower side of the inlet 71 of the steam channel 7. Outside of the impellor 8, there is a shell 81 which can guide the wind direction, the shape design of the shell 81 causes wind to blow upwards, the upper side of the shell 81 protruding upwards. On the protruding part there is a wind blowing mouth 810, which is connected with the said atomizing chamber 6 and is set near the inlet 71 of the steam channel 7.

The water of the water tank 5 enters atomizing chamber 6 through the water valve 9, being atomized to low temperature vapor by atomizer 61, being driven to passing the said steam channel 7, passing the steam pipe 3 and arriving the hand held part 1. The vapor is then heated by the heating unit in the handle 1 and finally ejected out from the steam outlet 110 of the handle 1 and cooperating with massage roller 13 to care the people's skin. Since the heating unit of the handle 1 is adjustable, the temperature of the ejecting steam can be controlled within the range which is suitable for the skin touching.

The water inlet valve 9 performs the water filling task automatically according to the followings: When the water level of the atomizing chamber 6 is lower than the void 91 and the channel is kept smoothly, the water of the water tank 5 will flow into atomizing chamber 6 through the water inlet valve 9. When the water level of the atomizing chamber 6 is higher than the void 91, since the water tank 5 is sealed, the inside of the chamber will generate negative pressure, and the water of the water tank 5 cannot flow into atomizing chamber 6.

The third embodiment is different from the second embodiment. The output part is a massage belt, on the inside surface of which there are several massage protruding points and a plurality of steam outlets which are respectively set between the corresponding massage protruding points. The heating unit is set on the outside surface of the massage belt, the heating unit comprising: a metal pipe tie-in, the two ends of which are connected with the steam pipe, a PTC heating element which is set on the outside wall of the metal pipe tie-in, and a thermostat which is connected with the PTC heating element. The atomization device and water tank are in a single body structure which is connected with the output part by steam pipe.

The output part of the present invention can also be other hairdressing tools, such as steam face shelter.

The above described features are only embodiments of the present invention. The design and idea of the present invention is not limited to these features, and equivalent changes and modifications based on the contents of the present invention fall within the scope of the present invention.

EXAMPLES

Example 1

Treatment of a Sleeping Disorder

Figure 4A:
FIGS. 4A and 4B show acupoints according to an embodiment of the present invention.
Figure 4B:
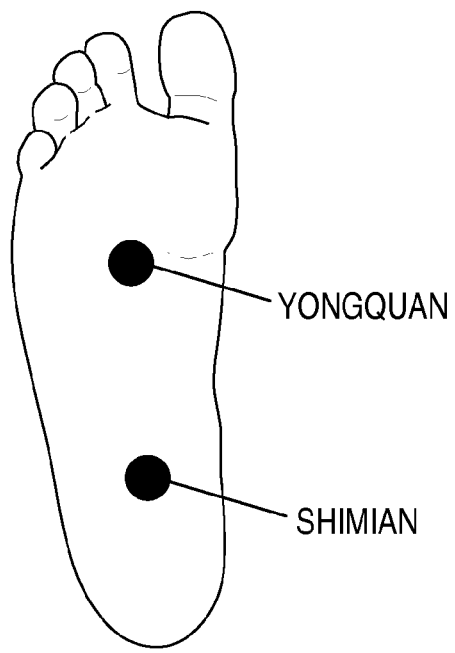

Patient Information
　Age: 40
　Gender: male
Symptom:
　Sleepless and awake until 2:30 am.
Treatment Protocol:
　Applying the hot vapor by the device of invention in each acupoint (FIGS. 4A and 4B) for 3 to 5 minutes, and, if necessary, repeat the process.
Acupoints
　Acupoints for insomnia according to the present example include Fengchi acupoints, shown in FIG. 4A, and Yongguan and Shimian acupoints, shown in FIG. 4B.
Results:
　Following the above described treatment, the patient was able to fall asleep normally until 7 o'clock in the morning.
Conclusion
　The present invention is effective for treating insomnia.

While particular embodiments of the present invention have been shown and described, it will be obvious to those skilled in the art that changes and modifications can be made without departing from this invention in its broader aspects. Therefore, the claims are to encompass within their scope all such changes and modifications as fall within the true sprit and scope of this invention.

I claim:

1. A method of providing treatment of a sleeping disorder of a patient, comprising:
　diagnosing the sleeping disorder of the patient;
　providing a steam forming device comprising:
　　(a) an atomization device comprising:
　　　an atomizing chamber comprising a low temperature vapor outlet,
　　　an atomizer located in the atomizing chamber and configured to make water in the atomizing chamber become a low temperature vapor, and
　　　an impeller configured to drive the low temperature vapor of the atomizing chamber into the outlet;
　　(b) a high temperature steam forming device configured for producing high temperature steam comprising a high temperature steam outlet;
　　(c) a steam outlet pipe, comprising:
　　　two steam intakes respectively connected with the low temperature vapor outlet of the atomizing chamber and the high temperature steam outlet of the high temperature steam forming device, and
　　　a mixing steam outlet; and
　　(d) a water tank configured for supplying needed water for the atomization device and the high temperature steam forming device;
　generating a low temperature vapor by passing a stream of water from the water tank through the atomization device;
　generating high temperature steam by passing another stream of water from the water tank through the high temperature steam forming device;
　creating a mixed vapor by mixing the high temperature steam and the low temperature vapor using the steam outlet pipe;
　adjusting the composition of the mixed vapor by adjusting the proportions of the high temperature steam and low temperature vapor; and
　improving a condition of the sleeping disorder or ameliorating the symptoms of the sleeping disorder by selectively applying a stream of mixed vapor of a temperature from 40° C. to 55° C. to a set of acupoints or an acupoint on the body of the patient using said steam forming device.

2. The method of claim 1, wherein the sleeping disorder is insomnia, and the acupoints comprise fengche, yongquan, and shimian.

3. The method of claim 1, wherein the low temperature vapor has a temperature of 45° C.

4. The method of claim 1, wherein the low temperature vapor has a temperature of 45° C. to 50° C.

5. The method of claim 1, wherein, in the steam forming device, the water tank comprises:
　a main water tank located on an upper side,
　an assistant water tank located on a lower side,
　a water inlet valve between the main water tank and the assistant water tank, and
　a wind guiding shell comprising a wind blowing mouth,
　wherein the atomizing chamber is set on one side of and connected with the assistant water tank;
　wherein the low temperature vapor outlet is set on top of the atomizing chamber;
　wherein the wind guiding shell is set outside of the impeller, the wind blowing mouth of the wind guiding shell faces a bottom of the low temperature vapor outlet; and
　wherein a water inlet pipe of the high temperature steam forming device is connected with a bottom of the assistant water tank where a water volume adjusting valve being set on a connecting area and the water volume adjusting valve comprises a knob which is adjustable outside.

6. The method of claim 5, wherein the steam forming device comprises a water inlet valve including a cylinder valve body which is protruding into the assistant water tank from a bottom of the water tank and a bottom edge,
　wherein the bottom edge of the valve comprises a void, the void being positioned lower than the wind blowing mouth;
　wherein the valve comprises a valve hole in a middle of a valve body;
　wherein in the valve hole there is a valve stopper which tightly fills the valve hole;

wherein the stopper comprises an up-extending valve stick on top of the stopper, the valve stick comprising a spring causing the valve stick to move up to tightly fill the valve hole; and wherein the main water tank comprises a water inlet on a top of the main water tank, the water inlet comprises a knob cover, a bottom of the water inlet comprising a connecting rod which extends into the main water tank and is capable of pushing the valve stick downward so as to cause the valve stopper to pull away from the valve hole.

7. The method of claim 1, wherein, in the steam forming device, the mixing steam outlet of a steam guiding output pipe is connected with a hollow ring by a steam pipe, wherein on a bottom of the hollow ring there are steam ejecting holes along the circumference of the ring, and wherein the hollow ring is set on a rack.

8. The method of claim 1, wherein, in the steam forming device, there is a heating unit located on a jointing position of a steam pipe and a hollow ring in the steam forming device, wherein the heating unit comprises:
a metal pipe tie-in comprising two ends, the two ends being connected with the steam pipe,
a PTC heating element set on an outside wall of the metal pipe tie-in, and
a thermostat which is connected with the PTC heating element.

9. The method of claim 8, wherein the steam forming device vapor and further comprises:
(e) an output part comprising a handling part, comprising:
a steam inlet on the handling part,
at least one steam outlet, and
a pipe connecting the steam inlet and the at least one steam outlet, wherein the pipe includes the heating unit; and
(f) a steam pipe which connects the steam inlet on the handling part with an low temperature steam outlet of the atomizing chamber,
wherein the temperature of said low temperature vapor is adjusted by the heating unit on the handling part.

10. The method of claim 9, wherein, in the steam forming device, the output part is the handling part, the handling part further comprising a head and a handle in a single body, the head comprising a plurality of massage rollers which are paratacticly set on the head,
wherein the handling part comprises a plurality of steam outlets which are respectively set between the corresponding massage rollers,
wherein the steam inlet on the handling part is set on an end of the handle; and
wherein the heating element is set inside the handle.

11. The method of claim 10, wherein, in the steam forming device, the atomizing chamber is located on a lower side of the water tank, the atomizing chamber being connected with outside atmosphere,
wherein the water tank is sealed,
wherein there is a water inlet valve between the water tank and the atomizing chamber, the water inlet valve including a cylinder valve body which is extending to the atomizing chamber where the inside of the valve body comprises a channel which connects the water tank with the atomizing chamber, and where a lower end of the valve body comprises a void,
wherein the atomizing chamber is connected with the steam outlet pipe by a steam channel, an inlet of the steam channel being positioned higher than the void of the water inlet valve,
wherein on the outside of the impeller there is a wind guiding shell, the wind guiding shell comprising a wind blowing mouth which is connected with the atomizing chamber and is near the inlet of the steam channel.

12. The method of claim 9, wherein, in the steam forming device, the atomizing chamber is located on a lower side of the water tank, the atomizing chamber being connected with outside atmosphere,
wherein the water tank is sealed,
wherein there is a water inlet valve between the water tank and the atomizing chamber,
the water inlet valve including a cylinder valve body which is extending to the atomizing chamber where the inside of the valve body comprises a channel which connects the water tank with the atomizing chamber, and where a lower end of the valve body comprises a void,
wherein the atomizing chamber is connected with the steam outlet pipe by a steam channel, a position of an inlet of the steam channel being higher than the void of the water inlet valve,
wherein on the outside of the impeller there is a wind guiding shell, the wind guiding shell comprising a wind blowing mouth which is connected with the atomizing chamber and is near the inlet of the steam channel.

13. The method of claim 9, wherein, in the steam forming device, the output part is a massage belt, on an inside surface of which there are several massage protruding points and a plurality of steam outlets which are respectively set between the corresponding massage protruding points, wherein the heating unit is set on an outside surface of the massage belt.

14. The method of claim 9, wherein, in the steam forming device, the atomization device and the water tank are a single body structure which is connected with the output part by the steam pipe.

15. The method of claim 1, wherein a treatment period is from about 1 minute to about 1 hr.

16. The method of claim 1, wherein a course of treatment is 1 month.

17. The method of claim 1, wherein a course of treatment is 6 months.

* * * * *